(12) United States Patent
Coquerel et al.

(10) Patent No.: US 8,067,639 B2
(45) Date of Patent: Nov. 29, 2011

(54) CRYSTALLINE FORM VI OF AGOMELATINE, A PROCESS FOR ITS PREPARATION AND PHARMACEUTICAL COMPOSITIONS CONTAINING IT

(75) Inventors: Gerard Coquerel, Boos (FR); Julie Linol, Rouen (FR); Lionel Le Pape, Gremonville (FR); Jean-Pierre Lecouve, Le Havre (FR)

(73) Assignee: Les Laboratoires Servier, Suresnes Cedex (FR)

( * ) Notice: Subject to any disclaimer, the term of this patent is extended or adjusted under 35 U.S.C. 154(b) by 625 days.

(21) Appl. No.: 12/291,143

(22) Filed: Nov. 6, 2008

(65) Prior Publication Data
US 2009/0069434 A1   Mar. 12, 2009

(30) Foreign Application Priority Data
Sep. 11, 2007   (FR) .................................... 07 07861

(51) Int. Cl.
*C07C 233/05* (2006.01)
*A61K 31/16* (2006.01)
(52) U.S. Cl. ........................................ 564/219; 514/630
(58) Field of Classification Search ................. 564/172, 564/219; 514/617, 630
See application file for complete search history.

(56) References Cited

U.S. PATENT DOCUMENTS

| 5,318,994 | A * | 6/1994 | Andrieux et al. | 514/613 |
|---|---|---|---|---|
| 6,849,120 | B2 * | 2/2005 | Singer et al. | 117/68 |
| 7,635,721 | B2 * | 12/2009 | Coquerel et al. | 514/630 |
| 7,645,905 | B2 * | 1/2010 | Coquerel et al. | 564/172 |
| 7,649,020 | B2 * | 1/2010 | Broquaire et al. | 514/618 |
| 7,910,625 | B2 * | 3/2011 | Coquerel et al. | 514/617 |
| 7,939,566 | B2 * | 5/2011 | Coquerel et al. | 514/630 |

FOREIGN PATENT DOCUMENTS

| EP | 044285 | 9/1991 |
| EP | 1564202 | 8/2005 |
| EP | 1752444 | 2/2007 |

OTHER PUBLICATIONS

Raminder Kumar, Drug, 2008, (13), 1803-1839.*
Depreux P. et al., "Synthesis and structure-activity relationships of novel naphthalenic and pioisosteric amidic derivatives as melatonin receptor ligands" Journal of Medicinal Chemistry, vol. 37, No. 20, p. 3231-3239. Sep. 30, 1994.
Tenant B., et al., "N-A2-(7-Methoxy-1-Naphthyl)Ethyluacetamide, A Prtent Melatonin Analog" Acta Crystallographica Section C. Crystal Structurecommunications, vol. C50, No. 6 p. 907-910, Jan. 1, 1994.
French Preliminary Search Report for FR0707861 of Jun. 30, 2008.

* cited by examiner

*Primary Examiner* — Shailendra Kumar
(74) *Attorney, Agent, or Firm* — Hueschen and Sage

(57) ABSTRACT

Crystalline form VI of the compound of formula (I):

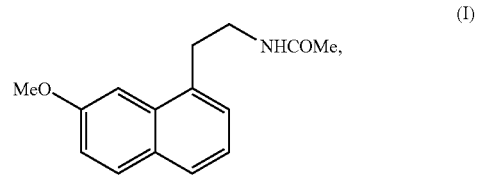

characterised by its X-ray powder diffraction diagram. Medicinal products containing the same which are useful in treating melatoninergic disorders.

10 Claims, No Drawings

CRYSTALLINE FORM VI OF AGOMELATINE, A PROCESS FOR ITS PREPARATION AND PHARMACEUTICAL COMPOSITIONS CONTAINING IT

The present invention relates to a new crystalline form, crystalline form VI, of agomelatine or N-[2-(7-methoxy-1-naphthyl)ethyl]acetamide, of formula (I):

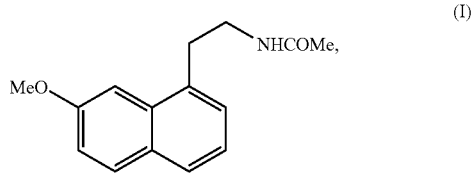

to a process for its preparation and to pharmaceutical compositions containing it.

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the 5-HT$_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent Specification EP 0 447 285.

In view of the pharmaceutical value of this compound, it has been of prime importance to obtain it with excellent purity and especially in a perfectly reproducible form that has valuable characteristics of dissolution and ease of formulation allowing its storage for long periods without particular requirements for temperature, light, humidity or oxygen levels.

The Applicant has now developed a process for obtaining agomelatine in a well-defined, reproducible crystalline form which as a result has valuable characteristics of dissolution and ease of formulation. This new form moreover has quite remarkable stability over time allowing optimum storage without particular precautions, which constitutes an advantage of prime importance in the pharmaceutical industry.

More specifically, the present invention relates to the crystalline form VI of the compound of formula (I), characterised by the following X-ray powder diffraction diagram, measured using a Bruker D5000matic diffractometer (copper anticathode) and expressed in terms of interplanar distance d, Bragg's angle 2 theta and relative intensity (expressed as a percentage relative to the most intense line):

| 2-Theta (°) exp. | d (Å) exp. | Intensity (%) |
|---|---|---|
| 5.73 | 15.411 | 11.4 |
| 10.22 | 8.645 | 11.6 |
| 20.10 | 4.413 | 10.2 |
| 23.69 | 3.751 | 59.0 |
| 29.48 | 3.027 | 14.8 |

The crystalline form VI of the compound of formula (I) has also been characterised by the following infra-red spectrum: peaks observed at 907.5 cm$^{-1}$; 866.7 cm$^{-1}$; 852.8 cm$^{-1}$; 827.4 cm$^{-1}$; 754.6 cm$^{-1}$; 734.6 cm$^{-1}$; 698.4 cm$^{-1}$; 672.1 cm$^{-1}$; 650.9 cm$^{-1}$; 611.9 cm$^{-1}$; 588.1 cm$^{-1}$.

The invention relates also to a process for the preparation of the crystalline form VI of the compound of formula (I), which process is characterised in that a solution of agomelatine in isopropyl ether is heated at boiling and then rapidly cooled to 0° C. After filtration in vacuo, form VI is obtained in pure form.

In the crystallisation process according to the invention it is possible to use the compound of formula (I) obtained by any process.

The invention relates also to another process for the preparation of the crystalline form VI of the compound of formula (I), which process is characterised in that agomelatine is crystallised from a water/ethanol mixture (50/50 volume/volume) at ambient temperature under high pressure for 24 hours.

Preference will be given, in that second crystallisation process according to the invention, to recrystallising agomelatine under a high pressure of 10 kbar.

In that second crystallisation process according to the invention it is possible to use the compound of formula (I) obtained by any process.

Obtaining this crystalline form has the advantage of allowing the preparation of pharmaceutical formulations that have a consistent and reproducible composition, having excellent stability over time.

Pharmacological study of form VI thereby obtained has shown substantial activity in respect of the central nervous system and microcirculation, enabling it to be established that the substance is useful in the treatment of stress, sleep disorders, anxiety, major depression, seasonal affective disorder, cardiovascular pathologies, pathologies of the digestive system, insomnia and fatigue due to jet-lag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and also in cerebral circulation disorders. In another field of activity, it appears that, in treatment, form VI of agomelatine can be used in sexual dysfunctions, that it has ovulation-inhibiting and immunomodulating properties and that it may potentially be used in the treatment of cancers.

Crystalline form VI of agomelatine will preferably be used in treating major depression, seasonal affective disorder, sleep disorders, cardiovascular pathologies, pathologies of the digestive system, insomnia and fatigue due to jet-lag, appetite disorders and obesity.

The invention relates also to pharmaceutical compositions comprising as active ingredient the crystalline form VI of the compound of formula (I) together with one or more appropriate, inert and non-toxic excipients. Among the pharmaceutical compositions according to the invention there may be mentioned, more especially, those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The useful dosage can be varied according to the nature and severity of the disorder, the administration route and the age and weight of the patient. The dosage varies from 0.1 mg to 1 g per day in one or more administrations.

The Examples hereinbelow illustrate the invention but do not limit it in any way.

EXAMPLE 1

Crystalline form VI of N-[2-(7-methoxy-1-naphthyl)ethyl]acetamide 0.74 g of N-[2-(7-methoxy-1-naphthyl)ethyl]acetamide and 36.06 g of isopropyl ether are introduced into a tube. This suspension is heated at boiling (at a temperature of 73° C.) for 2 hours. Rapid cooling to 0° C. is then carried out. After one hour at 0° C., filtration in vacuo over a porosity 3 glass frit is carried out. The solid obtained is characterised by its melting point and by the following X-ray powder diffraction diagram, measured using a Bruker D5000matic diffractometer (copper anticathode) and expressed in terms of interplanar distance d, Bragg's angle 2 theta and relative intensity (expressed as a percentage relative to the most intense line):

| 2-Theta (°) exp. | d (Å) exp. | Intensity (%) |
|---|---|---|
| 5.73 | 15.411 | 11.4 |
| 10.22 | 8.645 | 11.6 |
| 20.10 | 4.413 | 10.2 |
| 23.69 | 3.751 | 59.0 |
| 29.48 | 3.027 | 14.8 |

Melting point: 94° C.

Infra-red spectrum: 907.5 cm$^{-1}$; 866.7 cm$^{-1}$; 852.8 cm$^{-1}$; 827.4 cm$^{-1}$; 754.6 cm$^{-1}$; 734.6 cm$^{-1}$; 698.4 cm$^{-1}$; 672.1 cm$^{-1}$; 650.9 cm$^{-1}$; 611.9 cm$^{-1}$; 588.1 cm$^{-1}$.

EXAMPLE 2

Crystalline form VI of N-[2-(7-methoxy-1-naphthyl)ethyl]acetamide 2 g of N-[2-(7-methoxy-1-naphthyl)ethyl]acetamide are introduced into 20 ml of a water/ethanol mixture (50/50 volume/volume) at 25° C. This suspension is filtered over a porosity 4 glass frit. This saturated solution of N-[2-(7-methoxy-1-naphthyl)ethyl]-acetamide is subjected to a pressure of 10 kbar. After 24 hours, crystallisation is complete and the solid obtained is characterised by its melting point and by the following X-ray powder diffraction diagram, measured using a Bruker D5000matic diffractometer (copper anticathode) and expressed in terms of interplanar distance d, Bragg's angle 2 theta and relative intensity (expressed as a percentage relative to the most intense line):

| 2-Theta (°) exp. | d (Å) exp. | Intensity (%) |
|---|---|---|
| 5.73 | 15.411 | 11.4 |
| 10.22 | 8.645 | 11.6 |
| 20.10 | 4.413 | 10.2 |
| 23.69 | 3.751 | 59.0 |
| 29.48 | 3.027 | 14.8 |

Melting point: 94° C.

Infra-red spectrum: 907.5 cm$^{-1}$; 866.7 cm$^{-1}$; 852.8 cm$^{-1}$; 827.4 cm$^{-1}$; 754.6 cm$^{-1}$; 734.6 cm$^{-1}$; 698.4 cm$^{-1}$; 672.1 cm$^{-1}$; 650.9 cm$^{-1}$; 611.9 cm$^{-1}$; 588.1 cm$^{-1}$.

EXAMPLE 3

Pharmaceutical Composition

Formula for the preparation of 1000 tablets each containing 25 mg of active ingredient:

Compound of Example 1 or 2 . . . 25 g

Lactose monohydrate . . . 62 g

Magnesium stearate . . . 1.3 g

Maize starch . . . 26 g

Maltodextrins . . . 9 g

Anhydrous colloidal silica . . . 0.3 g

Pregelatinised maize starch, Type A . . . 4 g

Stearic acid . . . 2.6 g

EXAMPLE 4

Pharmaceutical Composition

Formula for the preparation of 1000 tablets each containing 25 mg of active ingredient:

Compound of Example 1 or 2 . . . 25 g

Lactose monohydrate . . . 62 g

Magnesium stearate . . . 1.3 g

Povidone . . . 9 g

Anhydrous colloidal silica . . . 0.3 g

Cellulose sodium glycolate . . . 30 g

Stearic acid . . . 2.6 g

The invention claimed is:

1. A crystalline form VI of agomelatine of formula (I):

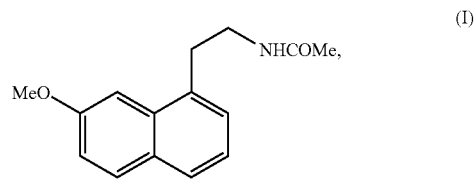

wherein the compound exhibits essentially the following X-ray powder diffraction diagram, measured using a diffractometer (copper anticathode) and expressed in terms of interplanar distance d, Bragg's angle 2 theta and relative intensity (expressed as a percentage relative to the most intense line):

| 2-Theta (°) exp. | d (Å) exp. | Intensity (%) |
|---|---|---|
| 5.73 | 15.411 | 11.4 |
| 10.22 | 8.645 | 11.6 |
| 20.10 | 4.413 | 10.2 |
| 23.69 | 3.751 | 59.0 |
| 29.48 | 3.027 | 14.8. |

2. A crystalline form VI of agomelatine of formula (I):

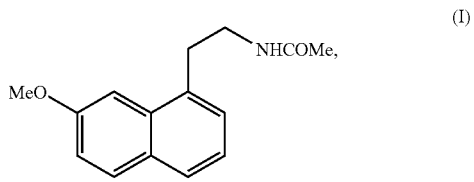

wherein the compound exhibits essentially the following infra-red spectrum: 907.5 cm$^{-1}$; 866.7 cm$^{-1}$; 852.8 cm$^{-1}$; 827.4 cm$^{-1}$; 754.6 cm$^{-1}$; 734.6 cm$^{-1}$; 698.4 cm$^{-1}$; 672.1 cm$^{-1}$; 650.9 cm$^{-1}$; 611.9 cm$^{-1}$; 588.1 cm$^{-1}$.

3. A process for the preparation of the crystalline form VI of the compound of formula (I) of claim 1, wherein a solution of agomelatine in isopropyl ether is heated at boiling, rapidly cooled to 0° C. and then filtered in vacuo.

4. A process for the preparation of the crystalline form VI of the compound of formula (I) of claim 2, wherein a solution of agomelatine in isopropyl ether is heated at boiling, rapidly cooled to 0° C. and then filtered in vacuo.

5. A process for the preparation of the crystalline form VI of the compound of formula (I) of claim 1, wherein agomelatine is crystallised from a water/ethanol mixture (50/50 volume/volume) at ambient temperature under high pressure for 24 hours.

6. A process for the preparation of the crystalline form VI of the compound of formula (I) of claim 2, wherein agomelatine is crystallised from a water/ethanol mixture (50/50 volume/volume) at ambient temperature under high pressure for 24 hours.

7. A pharmaceutical composition comprising as active ingredient the crystalline form VI of agomelatine of claim 1, in combination with one or more pharmaceutically acceptable, inert and non-toxic carriers.

8. A pharmaceutical composition comprising as active ingredient the crystalline form VI of agomelatine of claim 2, in combination with one or more pharmaceutically acceptable, inert and non-toxic carriers.

9. A method for treating sleep disorders in a subject in need thereof, comprising the step of administering a therapeutically effective amount of the crystalline form VI of agomelatine of claim 1.

10. A method for treating sleep disorders in a subject in need thereof, comprising the step of administering a therapeutically effective amount of the crystalline form VI of agomelatine of claim 2.

* * * * *